(12) United States Patent
Spivey et al.

(10) Patent No.: US 9,314,244 B2
(45) Date of Patent: Apr. 19, 2016

(54) DIRECTIONAL SURGICAL SUTURES

(71) Applicant: DePuy Mitek, LLC, Raynham, MA (US)

(72) Inventors: James Spivey, Canton, MA (US); Daniel Walsh, Boston, MA (US); Justin Piccirillo, Uxbridge, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 266 days.

(21) Appl. No.: 14/137,159

(22) Filed: Dec. 20, 2013

(65) Prior Publication Data

US 2015/0173753 A1  Jun. 25, 2015

(51) Int. Cl.
| | |
|---|---|
| *A61B 17/04* | (2006.01) |
| *A61B 17/06* | (2006.01) |
| *A61B 17/00* | (2006.01) |
| *D01D 5/00* | (2006.01) |
| *A61B 19/00* | (2006.01) |

(52) U.S. Cl.
CPC ....... *A61B 17/06166* (2013.01); *A61B 17/0466* (2013.01); *A61B 2017/00526* (2013.01); *A61B 2017/06171* (2013.01); *A61B 2017/06185* (2013.01); *A61B 2019/444* (2013.01); *A61B 2019/446* (2013.01); *D01D 5/00* (2013.01)

(58) Field of Classification Search
None
See application file for complete search history.

(56) References Cited

U.S. PATENT DOCUMENTS

| | | | |
|---|---|---|---|
| 2,809,458 A | 10/1957 | Wilbourn | |
| 3,762,418 A | 10/1973 | Wasson | |
| 3,949,755 A | 4/1976 | Vauquois | |
| 4,179,160 A | 12/1979 | Sabo | |
| 4,844,000 A | 7/1989 | Clement | |
| 5,027,741 A | 7/1991 | Smith et al. | |
| 5,217,027 A | 6/1993 | Hermens | |
| 5,368,599 A | 11/1994 | Hirsch et al. | |
| 5,489,294 A | 2/1996 | McVenes et al. | |
| 5,536,273 A | 7/1996 | Lehrer | |
| 5,651,377 A | 7/1997 | O'Donnell, Jr. | |
| 5,746,754 A | 5/1998 | Chan | |
| 5,810,849 A | 9/1998 | Kontos | |
| 5,830,125 A | 11/1998 | Scribner et al. | |
| 5,983,949 A | 11/1999 | Pohle | |
| 6,599,310 B2 | 7/2003 | Leung et al. | |
| 6,994,719 B2 | 2/2006 | Grafton | |
| 7,029,490 B2 | 4/2006 | Grafton et al. | |
| 7,331,311 B2 | 2/2008 | Hurwitz | |
| 8,012,172 B2 | 9/2011 | Grafton et al. | |
| 8,092,856 B2 | 1/2012 | Hadba | |
| 8,114,128 B2 | 2/2012 | Cauldwell et al. | |

(Continued)

OTHER PUBLICATIONS

Popper. "Braiding." *Handbook of Composite Reinforcements*. Lee, ed. (1992):24-40.

*Primary Examiner* — Robert Lynch

(57) ABSTRACT

Surgical sutures are provided. In general, the surgical sutures can include a plurality of directional indicators that each visually indicate a same direction, e.g., a direction toward one free end of the suture. The directional indicators can be configured to indicate a position of the suture relative to a patient and/or other medical device(s). The directional indicators can be a function of the suture itself so as to be an integral part thereof. In other words, threads, also referred to as "strands," that form the suture can define the directional indictors. The suture can be braided using threads of two different colors so as to form the directional arrows as an integral part of the suture when the suture is braided in manufacturing of the suture.

20 Claims, 6 Drawing Sheets

(56) References Cited

U.S. PATENT DOCUMENTS

| | | |
|---|---|---|
| 8,202,564 B2 | 6/2012 | Hadba |
| 8,239,008 B2 | 8/2012 | Voegele et al. |
| 2002/0151932 A1 | 10/2002 | Bryant et al. |
| 2005/0004601 A1 | 1/2005 | Kong et al. |
| 2005/0033362 A1 | 2/2005 | Grafton |
| 2005/0119696 A1 | 6/2005 | Walters et al. |
| 2007/0005110 A1 | 1/2007 | Collier et al. |
| 2007/0048554 A1 | 3/2007 | Jacobs et al. |
| 2007/0202286 A1 | 8/2007 | Jacobs et al. |
| 2008/0132942 A1 | 6/2008 | Mueller |
| 2009/0048627 A1 | 2/2009 | Hadba |
| 2009/0312791 A1 | 12/2009 | Lindh, Sr. et al. |
| 2010/0217316 A1 | 8/2010 | Fedinec |
| 2011/0082478 A1 | 4/2011 | Glick et al. |
| 2011/0264138 A1 | 10/2011 | Avelar et al. |
| 2011/0319932 A1 | 12/2011 | Avelar et al. |
| 2012/0073064 A1 | 3/2012 | Hadba |
| 2012/0232589 A1 | 9/2012 | Fedinec |
| 2013/0296934 A1 | 11/2013 | Sengun |

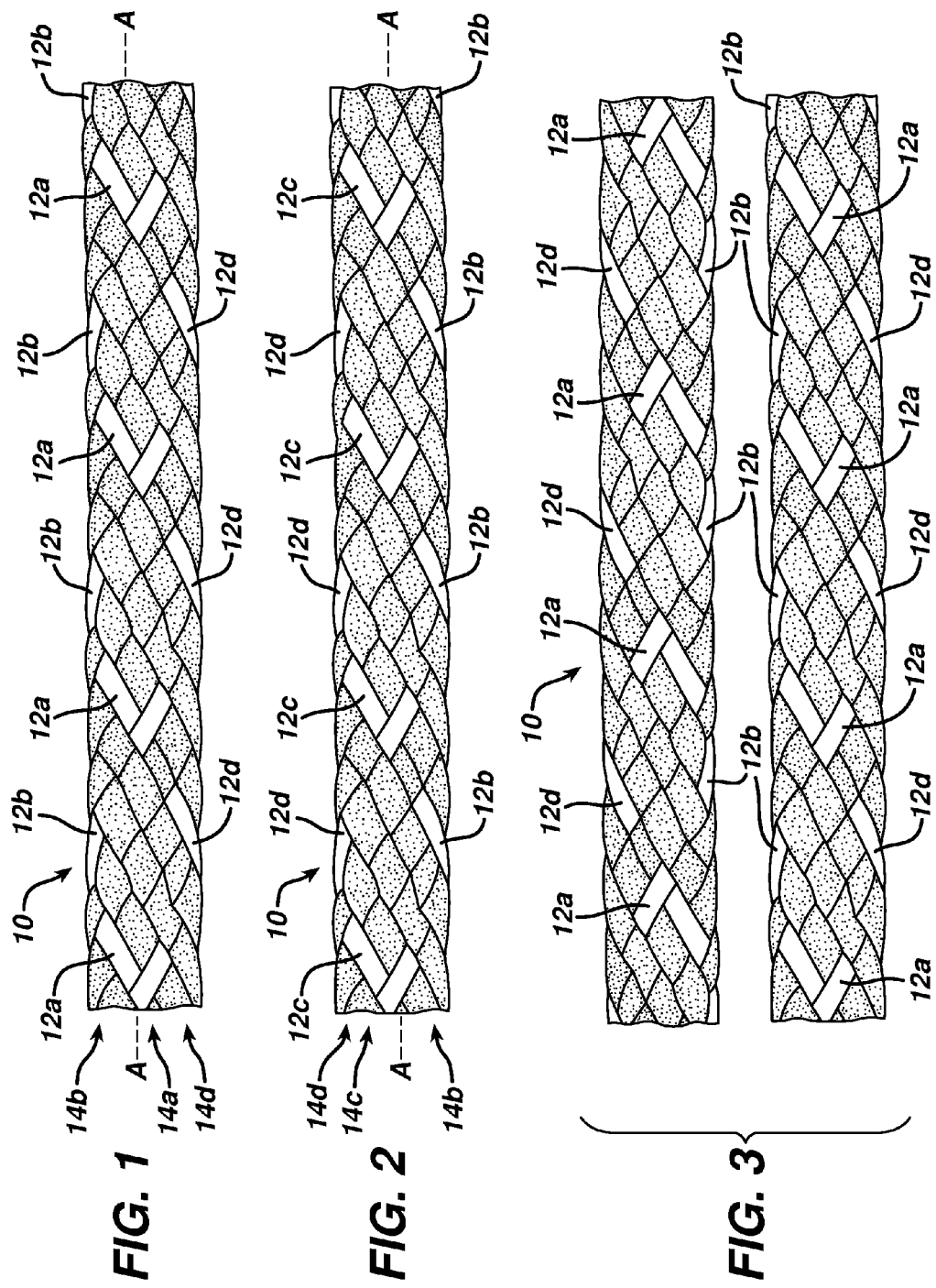

DIRECTIONAL SURGICAL SUTURES

FIELD

The present disclosure relates generally to surgical sutures, and more particularly to directional surgical sutures.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks.

One or more sutures are typically used in soft tissue repair procedures with devices for tissue attachment to secure the tissue in a desired location. The sutures are typically disposed through one or more portions of the tissue to be repaired, one or more devices for tissue attachment, and/or one or more tissues adjacent to the tissue to be repaired. The suture(s) are typically tensioned to position and hold the element(s) through which the suture(s) are disposed in desired positions relative to one another to facilitate healing of the damaged tissue. However, it can be difficult and/or time consuming to determine which direction to pass the suture(s) through the tissue and/or other element(s) and/or which direction to tension the suture(s). For example, when the suture(s) are being used in an arthroscopic procedure, only a small portion of the suture(s) may be visible arthroscopically, and at least some element(s) through which the suture(s) pass may not be visible at all when the suture(s) are being threaded and/or tensioned. It can therefore be difficult and/or time consuming to determine which direction to pass and/or tension the suture. For another example, when a suture is looped through tissue and/or another element such that two or more limbs of the suture extend from the tissue and/or other element, it can be difficult and/or time consuming to determine which one of the limbs to tension when all of the limbs are part of the same suture and hence all look the same as one another. Similarly, when multiple sutures that look the same are all in use, it can be difficult and/or time consuming to determine which of the sutures to tension, at all or in a certain order, and in which direction to tension the sutures even after the proper suture for tensioning has been identified.

In addition to being used in soft tissue repair procedures, sutures are also used in other medical procedures, such as in closing skin surface wounds and in various aspects of cosmetic surgery. Similar to that discussed above regarding sutures in soft tissue repair procedures, it can be difficult and/or time consuming to determine which direction to pass sutures through tissue and/or other material and/or which direction to tension the sutures when performing these other medical procedures.

Accordingly, there remains a need for improved surgical sutures.

SUMMARY

In one embodiment, a surgical device is provided that includes a suture configured to engage tissue of a patient. The suture can include a first plurality of threads of a first color and a second plurality of threads of a second color. The first plurality of threads can be braided with the second plurality of threads such that directional arrows formed only from the second plurality of threads are present on an external surface of the suture and are visually discernable by a human user of the suture. All of the directional arrows can point in a same direction.

The suture can vary in any number of ways. For example, the directional arrows can include a first row of directional arrows longitudinally aligned along a longitudinal length of the suture and a second row of directional arrows longitudinally aligned along the longitudinal length of the suture. For another example, the first and second rows can be positioned 180° apart from one another around a circumference of the suture. For yet another example, the directional arrows can include a third row of directional arrows longitudinally aligned along the longitudinal length of the suture and a fourth row of directional arrows longitudinally aligned along the longitudinal length of the suture. In some embodiments, the first, second, third, and fourth rows can be positioned 90° apart from adjacent ones of the rows around a circumference of the suture. For another example, a number of the first plurality of threads can be greater than a number of the second plurality of threads, e.g., the number of the first plurality of threads can be three times the number of the second plurality of threads. For still another example, the directional arrows can be the only portion of the external surface of the suture formed by the second plurality of threads. For another example, the suture can be flexible.

The suture can be used in a surgical method that in one embodiment includes coupling the suture to the tissue such that first and second free lengths of the suture extend from the tissue. The first free length can have the directional arrows thereon pointing toward the tissue and the second free length having the directional arrows thereon can point away from the tissue. The method can also include, after coupling the suture to the tissue, pulling the second free length of the suture in the direction in which the directional arrows thereon point so as to tighten the suture relative to the tissue.

In another embodiment, a surgical device includes a suture configured to engage tissue of a patient. The suture can including a first plurality of threads of a first color and a second plurality of threads of a second color that visually contrasts with the first color. The first plurality of threads can be braided with the second plurality of threads such that the second plurality of threads form a pattern of arrows on an external surface of the suture. All of the arrows can point in a same direction toward one free end of the suture. The second color visually contrasting with the first color can allow the plurality of arrows to be visually discernable by a human user of the suture.

The suture can have any number of variations. For example, the directional arrows can be an integral part of the suture and can be formed only from the second plurality of threads. For another example, the arrows can include a plurality of rows of arrows. The arrows in each of the rows can be longitudinally aligned along a longitudinal length of the suture. The rows can be spaced equidistantly from each other around a circumference of the suture. For yet another example, the pattern of arrows can be the only portion of the external surface of the suture formed by the second plurality of threads. For still another example, the suture can be flexible.

The suture can be used in a surgical method that in one embodiment includes coupling the suture to the tissue such that first and second free lengths of the suture extend from the tissue. The first free length can have the arrows thereon pointing toward the tissue. The second free length can have the arrows thereon pointing away from the tissue. The one free end of the suture can be a terminal end of the second free length of the suture. The method can also include, after coupling the suture to the tissue, pulling the second free length of the suture in the direction in which the arrows thereon point so as to tighten the suture relative to the tissue.

In another aspect, a method of creating a suture is provided that in one embodiment includes braiding a first plurality of threads of a first color with a second plurality of threads of a second color so as to create a suture configured to engage tissue of a patient. The suture can have a plurality of arrows on an external surface thereof that are entirely formed with the second plurality of threads. All of the arrows can point in a same direction. The braiding can use a plurality of gears. The gears can be arranged around a perimeter of a shape such that each of the gears is adjacent to two others of the gears. Each of the gears can rotate in an opposite direction to its two adjacent gears when braiding the suture. Each of the gears can seat at least one bobbin having one of the threads wound therearound. An even number of the bobbins can be wound with the second plurality of threads, and a remaining number of the bobbins can be wound with the first plurality of threads. The gears can be arranged around the perimeter of the shape in an order of half the gears including at least one of the bobbins wound with the second plurality of threads, half the gears including at least one of the bobbins wound with the first plurality of threads and no bobbins wound with the second plurality of threads, the other half of the gears including at least one of the bobbins wound with the second plurality of threads, and the other half of the gears including at least one of the bobbins wound with the first plurality of threads and no bobbins wound with the second plurality of threads.

The method can vary in any number of ways. For example, a ratio of the even number of the bobbins to the remaining number of the bobbins can be 1:3.

In another aspect, a medical device is provided that includes the suture formed by the method of creating a suture.

BRIEF DESCRIPTION OF DRAWINGS

This invention will be more fully understood from the following detailed description taken in conjunction with the accompanying drawings, in which:

FIG. 1 is a side view of one embodiment of a suture that includes directional indicators;

FIG. 2 is a side view of the suture of FIG. 1 rotated 180° about a longitudinal axis of the suture;

FIG. 3 is a side view of the suture of FIG. 1 in a "U" shape with two limbs of the suture being positioned side-by-side;

DETAILED DESCRIPTION

Figure 4:
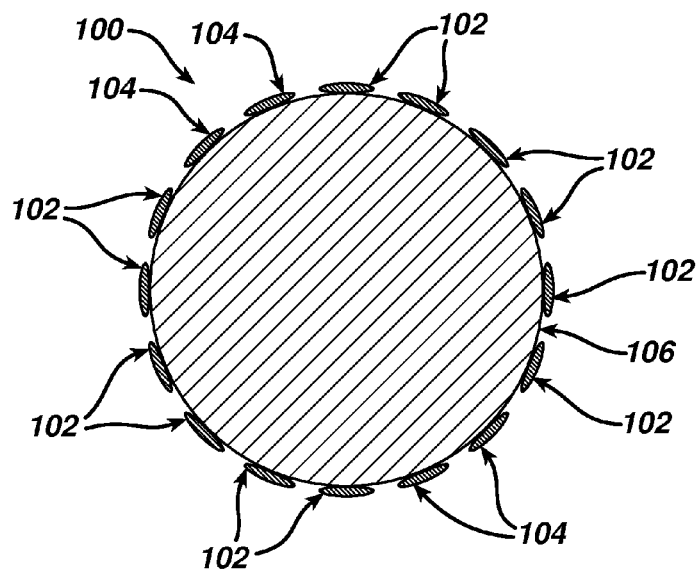
FIG. 4 is a cross-sectional schematic view of one embodiment of a suture that includes directional indicators and a core.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary surgical sutures are provided. In general, the surgical sutures can include a plurality of directional indicators that each visually indicate a same direction, e.g., a direction toward one free end of the suture. The directional indicators can be configured to indicate a position of the suture relative to a patient and/or other medical device(s). The directional indicators can be a function of the suture itself so as to be an integral part thereof. In other words, threads, also referred to as "strands," that form the suture can define the directional indictors. The suture can be braided using threads of two different colors so as to form the directional arrows as an integral part of the suture when the suture is braided in manufacturing of the suture, as discussed further below. In one embodiment, a surgical suture can include a plurality of directional indicators aligned along a longitudinal length of the suture such that the suture includes a row of directional indicators that extend along the longitudinal length of the suture. In an exemplary embodiment, the suture can include a plurality of rows of directional indicators along its longitudinal length. The plurality of rows can be arranged radially around the suture's circumference, e.g., rows 90° apart from one another or rows 180° degrees apart from one another, which can facilitate a user's visual observation of the directional indicators regardless of the user's vantage point of the suture.

The directional indicators can help indicate the suture's positional relationship relative to tissue of a patient and/or relative to one or more medical devices used in a medical procedure. Knowing the suture's positional relationship to the tissue and/or the medical device(s) can facilitate determination of which direction to pull the suture so that the suture is tensioned in the correct direction to produce a desired result, e.g., tensioning two tissues together, sliding the suture through a passageway extending through a cannula, trocar, bone anchor, or other medical device, passing the suture through a tissue, etc. The directional indicators can facilitate efficiency of the medical procedure by a user being able to easily visually observe the directional indicators and consequently know the suture's position relative to the tissue and/or the medical device(s) without the suture being unnecessarily moved relative to the tissue and/or the medical device(s) to determine the suture's position, which takes time and can cause the suture, the tissue, and/or the medical device(s) to shift from a desired position so as to require readjustment. Additionally, multiple sutures can be in use at the same time during a medical procedure. It can be difficult to determine which suture to pull from among the multiple sutures and to determine which direction to pull the suture even after the proper suture is identified. By using a suture with directional indicators in the medical procedure among other, different sutures (e.g., sutures without directional indicators and/or sutures with directional indicators but of different colors), the correct suture to pull and its proper pulling direction can be easily identified.

Whether a suture is the only one being used or is one among a plurality of sutures being used, in some medical procedures, the suture can pass into and out of tissue and/or a medical device such that both free ends of the suture are available for manipulation. It can be difficult to determine which one of the free ends to pull since the free ends can look identical to one another, as being part of the same suture. The suture having directional indicators can facilitate identification of the correct free end to be pulled since the indicators can visually show the direction to pull the suture.

The sutures disclosed herein can be used in a variety of medical procedures. Although the sutures disclosed herein can be used in a non-surgical context, in an exemplary embodiment, the sutures disclosed herein can be used in surgical procedures. For example, a suture having directional indicators can be used in surgical procedures in which a graft is secured within a tunnel formed in a bone, such as a procedure for attaching tissue to bone, e.g., anterior cruciate ligament (ACL) repair, rotator cuff repair, etc. In an exemplary embodiment, a surgical procedure including use of a suture having directional indicators can be a minimally invasive procedure, but as will be appreciated by a person skilled in the art, the sutures disclosed herein also have application in open surgical instrumentation as well as application in robotic-assisted surgery.

In an exemplary embodiment, a suture having directional indicators can be configured to be used in a surgical procedure that includes implanting a bone anchor, also referred to as a "suture anchor," within a patient to facilitate attachment of tissue to bone. The bone anchor can have a variety of sizes, shapes, and configurations. In an exemplary embodiment, the bone anchor can be cannulated and can include a suture-engaging member formed therein and configured to receive a suture therearound such that trailing ends of the suture can extend through the suture anchor. Examples of cannulated bone anchors with suture-engaging members include the Healix™ anchor and the Gryphon™ anchor available from Depuy Mitek, Inc. of Raynham, Mass., and the bone anchors described in U.S. Pat. No. 8,114,128 entitled "Cannulated Suture Anchor" issued Feb. 14, 2012 and in U.S. Pat. Pub. No. 2013/0296934 entitled "Systems, Devices, And Methods For Securing Tissue Using Snare Assemblies And Soft Anchors" filed May 7, 2012.

FIGS. 1-3 illustrate one embodiment of a suture 10 that includes a plurality of directional indicators 12a, 12b, 12c, 12d. FIG. 2 shows the suture 10 rotated 180° about its longitudinal axis A from the suture 10 of FIG. 1. FIG. 3 shows two lengths of the suture 10 side-by-side when the suture 10 is in a "U" shape with free ends (not shown) of the suture 10, e.g., terminal ends of the "U," positioned on a left side of FIG. 3 and with a bent intermediate portion (not shown) of the suture 10, e.g., a curved bottom of the "U," positioned on a right side of FIG. 3.

The directional indicators 12a, 12b, 12c, 12d in the illustrated embodiment include arrows each having a "V" shape. Each of the arrows 12a, 12b, 12c, 12d can point in a same direction, e.g., toward a same free end (not shown) of the suture 10, as shown in FIGS. 1-3. The arrows 12a, 12b, 12c, 12d can be arranged in a plurality of rows 14a, 14b, 14c, 14d that each extend longitudinally along an entire longitudinal length of the suture 10. The arrows 12a, 12b, 12c, 12d can be identical to one another. The arrows 12a, 12b, 12c, 12d in different ones of the rows 14a, 14b, 14c, 14d are identified by different reference numeral suffixes, e.g., suffix "a" for arrows 12a in a first one of the rows 14a, suffix "b" for arrows 12b in a second one of the rows 14b, etc. Although the suture 10 in the illustrated embodiment includes four rows 14a, 14b, 14c, 14d of directional indictors 12a, 12b, 12c, 12d, a suture can include any number of rows of directional indicators. In an exemplary embodiment, a suture can include an even number of rows of directional indicators.

The rows 14a, 14b, 14c, 14d can be arranged equidistantly from one another around the suture's circumference. As in the illustrated embodiment, the suture's four rows 14a, 14b, 14c, 14 can be spaced 90° apart from one another around the suture's circumference. In another embodiment including, for example, two rows of directional indicators, the two rows can be spaced 180° apart from one another around the suture's circumference. A person skilled in the art will appreciate that even though the rows may not be precisely equidistantly spaced from one another due to, for example, manufacturing tolerances in thread widths, the rows can nevertheless be considered to be equidistantly spaced from one another.

Each of the arrows 12a, 12b, 12c, 12d in a same one of the rows 14a, 14b, 14c, 14d can be longitudinally aligned with one another, e.g., the arrows 12a in the first row 12a being longitudinally aligned as shown in FIGS. 1 and 3, the arrows 12b in a second one of the rows 12b being longitudinally aligned as shown in FIGS. 1-3, etc. Ones of the arrows 12a, 12b, 12c, 12d in adjacent ones of the rows 14a, 14b, 14c, 14d can be axially offset from one another, e.g., the arrows 12a in the first row 12a being radially offset from the arrows 12b, 12d in the second and fourth rows 14b, 14d as shown in FIGS. 1 and 3, the arrows 12b in the second row 14b being radially offset from the arrows 12a, 12c in the first and third rows 14a, 14c as shown in FIGS. 1 and 3, etc. Thus, rows that are spaced 180° apart from one another around the circumference of the suture 10, e.g., the first and third rows 14a, 14c and the second and fourth rows 14b, 14d, can have arrows that are axially aligned with one another.

The directional indicators 12a, 12b, 12c, 12d can be configured to be visually discernable by a user of the suture 10. In an exemplary embodiment, the directional indicators 12a, 12b, 12c, 12d can form a partial portion of an external surface of the suture 10, as discussed further below.

The directional indicators 12a, 12b, 12c, 12d can be integral parts of the suture 10. In other words, the directional indicators 12a, 12b, 12c, 12d can be a function of the suture 10. The suture 10 can thus provide a directional indication thereof without a supplemental element, an appliqué, a written marking, stitching, etc., being applied thereto after the suture 10 has already been formed or at any time during the suture's manufacturing.

The suture 10 can be formed from a plurality of threads. The plurality of threads can define the directional indicators 12a, 12b, 12c, 12d. In other words, the material forming the suture 10 itself can define the directional indicators 12a, 12b, 12c, 12d. The threads that form the suture 10 can be made from any one or more materials, as will be appreciated by a person skilled in the art. In an exemplary embodiment, the threads can be a biocompatible material and can be flexible. The threads being flexible can allow the suture 10 to be flexible, as in the illustrated embodiment. The threads can be natural or synthetic, and can be absorbable or non-absorbable. Examples of materials for the threads include polymers, such as polyglycolide, polypropylene, polyethylene teretphalate (PET), and polydioxanone, and fabrics, such as nylon and silk. The threads that form the suture 10 can made from different materials, e.g., a first number of the threads being nylon and a second number of the threads being PET.

A first number of the threads can be a first color, and a second, remaining number of the threads can be a second color. A background of the suture 10 can be formed from the threads of the first color, and the directional indicators 12a, 12b, 12c, 12d can be formed from the threads of the second color. The background of the suture 10 generally refers to an external surface of the suture 10 that does not include the directional indicators 12a, 12b, 12c, 12d. The first and second colors can highly contrast with one another, which can facilitate visualization of the directional indicators 12a, 12b, 12c, 12d against the background. Examples of first and second colors, expressed as first color/second color, include white/black, black/white, blue/white, white/blue, purple/white, white/purple, yellow/black, black/yellow, blue/yellow, yellow/blue, purple/yellow, yellow/purple, pink/black, pink/white, blue/pink, pink/blue, purple/pink, and pink/purple, although a suture can be formed from different color contrast pairs. In an exemplary embodiment, the threads of the first color can be opaque, which can help prevent any threads of the second color underlying threads of the first color from being visible through the threads of the first color and thereby facilitate visualization of the directional indicators formed by the threads of the second color. In an exemplary embodiment, the second color can be the lighter one of the first and second colors such that the directional indicators 12a, 12b, 12c, 12d are lighter than the background, which can help prevent any threads of the second color underlying threads of the first color from being visible through the threads of the first color and thereby facilitate visualization of the directional indicators formed by the threads of the second color. In the illustrated embodiment of FIGS. 1-3, the first color is black, and the second color is white.

In an exemplary embodiment, the first and second colors are solid, as in the illustrated embodiment. Alternatively, one or both of the first and second threads can be patterned while still maintaining a general color scheme of two colors. For example, the second number of the threads can be white with a dyed stripe pattern of another color.

The threads of the first color and the threads of the second color can each have the same denier. Alternatively, a denier of threads of one the first and second colors can be greater than a denier of threads of the other one the first and second colors. For example, a denier of the threads of the first color can be greater than a denier of the threads of the second color, which can help prevent any threads of the second color underlying threads of the first color from being visible through the threads of the first color and thereby facilitate visualization of the directional indicators formed by the threads of the second color.

The threads of the first and second colors can made from different materials, e.g., threads of the first color being PET and threads of the second color being nylon, or the threads of the first and second color can all be made from the same material, e.g., nylon.

The threads can each have any diameter. Each of the threads can have a same diameter, which can help the suture have a uniform diameter along its longitudinal length. As will be appreciated by a person skilled in the art, the size of the threads' diameters can define the diameter of the suture, e.g., larger diameter threads result in a larger diameter suture. In some embodiments, a diameter of threads of one the first and second colors can be greater than a diameter of threads of the other one the first and second colors. For example, a diameter of the threads of the first color can be greater than a diameter of the threads of the second color, which can help prevent any threads of the second color underlying threads of the first color from being visible through the threads of the first color and thereby facilitate visualization of the directional indicators formed by the threads of the second color.

In some embodiments, one of the first and second threads can be configured to fluoresce, Having one of a suture's first and second threads, e.g., the second threads forming the directional indicators, configured to fluoresce can facilitate visualization of the directional indicators, even when the suture is disposed in a relatively dark area and/or no external light source is available. The fluorescence can be provided in any of a variety of ways, as will be appreciated by a person skilled in the art, such as by the one of the first and second threads including fluorescent nanoparticles, e.g., the fluorescent nanoparticles discussed in U.S. Pat. No. 8,239,008 entitled "Sentinel Node Identification Using Fluorescent Nanoparticles" issued Aug. 7, 2012.

A number of the first color threads can vary, and a number of the second color threads can also vary. A ratio of the number of the first threads to the number of the second threads can be three to one. In an exemplary embodiment, there are an even number of threads of the second color so as to allow the threads of the second color to form an arrow having a "V" shape. Using an odd number of threads of the second color can allow the one of the threads of the second color without a paired thread of the second color to form an arrow without a head, e.g., form a slash mark "/" or "\" shape. In the illustrated embodiment, the threads have a three to one ratio with the suture 10 including twelve threads of the first color and four threads of the second color. A number of threads of the second color can define a number of the suture's rows 14a, 14b, 14c, 14d. Thus, by the suture of FIGS. 1-3 having twelve and four of the first and second threads, respectively, the suture 10 has four rows 14a, 14b, 14c, 14d of directional indicators 12a, 12b, 12c, 12d. Although the suture 10 in the illustrated embodiment is formed from a total of sixteen threads, a suture including directional indicators can be formed from another number of threads. In another embodiment in which a suture has a three to one ratio of first threads to second threads, six threads of the first color and two threads of the second color can result in a suture having two rows of directional indicators.

As in the illustrated embodiment, threads of only two colors can be visible on an exterior surface of the suture 10, with the suture's background being formed of the threads of the first color and the suture's directional indicators 12a, 12b, 12c, 12d being formed of the threads of the second color. The directional indicators 12a, 12b, 12c, 12d can be the only portion of the suture's external surface formed by the threads of the second color, and the background of the suture 10 can be the only portion of the suture's external surface formed by the threads of the first color. Having only two colors visible on the suture's exterior surface can facilitate visual identification of the directional indicators 12a, 12b, 12c, 12d by helping to contrast the color of the directional indicators 12a, 12b, 12c, 12d with the different color of the suture's background.

A suture can include threads of more than two colors. For example, a suture can include a first number of threads of a first color, a second number of threads of a second color, and a third, remaining number of threads of a third color. The first color can form the suture's background, and the second and third colors can form the suture's directional indicators. Accordingly, the first color can highly contrast with the second and third colors. All of the directional indicators in a same row can have the same color. In this way, every other row around the suture's circumference can have directional indicators of a different color. The directional indicators can thus facilitate determination of the suture's rotational orientation through visual observation of which one or more of the rows are visible from a certain visual perspective, e.g., whether a row of directional indicators of the second color is most clearly visible or whether a row of directional indicators of the third color is most clearly visible.

The suture 10 can have a core (not shown) around which the threads are arranged to form the suture 10. The core can be configured to provide stability to the suture 10, as will be appreciated by a person skilled in the art. The core can be formed from any one or more materials, such as a polymer or a fabric. The core can be transparent, which can help prevent the core from interfering with a color scheme of the threads should any portion of the core be visible between the threads wrapped, woven, braided, etc. therearound. In an exemplary embodiment, the core can be a monofilament.

The suture 10 can be braided. The plurality of threads of the first and second colors that form the suture 10 can be braided together to form the suture 10. If the suture includes a core, the threads can be braided around the core. In an exemplary embodiment, a braiding machine can be loaded with the plurality of threads of the first and second colors and can braid the plurality of threads together to form the suture 10. An arrangement of the first color threads and the second color threads on the braiding machine relative to one another can allow the directional indicators 12a, 12b, 12c, 12d to be formed during the braiding process, as discussed further below.

The suture 10 can include one or more barbs (not shown) thereon that point in a same direction as the directional indicators 12a, 12b, 12c, 12d such that pulling a first free end of the suture 10, toward which the barbs and the directional indicators 12a, 12b, 12c, 12d point, can allow the one or more barbs to easily pass through the tissue(s), as opposed to pulling a second, opposite free end of the suture 10. Examples of sutures including one or more barbs that can include directional indicators include the barbed sutures discussed in U.S. Pat. Pub. No. 2009/0312791 entitled "Collapsible Barbed Sutures Having Reduced Drag And Methods Therefor" filed Jun. 17, 2008, and U.S. Pat. Pub. No. 2007/0005110 entitled "Braided Barbed Suture" filed Jun. 29, 2005.

FIG. 4 illustrates another embodiment of a suture 100 that includes a plurality of directional indicators (not shown) in the form of arrows having a "V" shape. The suture 100 can be formed from a plurality of threads 102 of a first color that form a background of the suture 100 and a plurality of threads 104 of a second, different color that form the directional indicators. The suture 100 in this illustrated embodiment includes a core 106 around which the threads 102, 104 are braided. The core 106 in this illustrated embodiment is a monofilament that is transparent and made from PET, but as mentioned above, the core of a suture can include multiple strands, can have a color, and can be made from any one or more materials.

Figure 5:
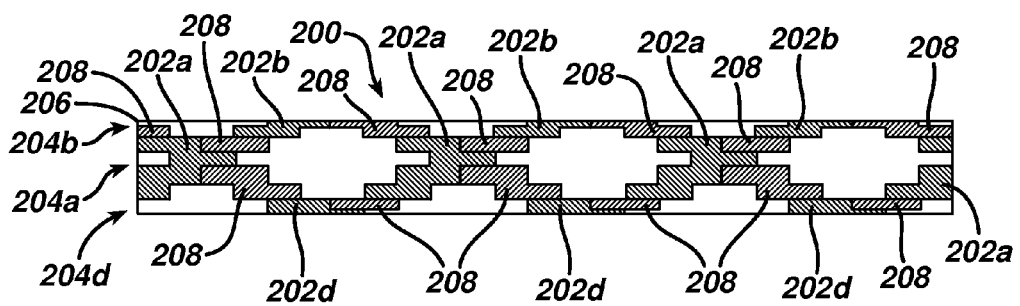
FIG. 5 is a side schematic view of another embodiment of a suture that includes directional indicators.

FIG. 5 illustrates another embodiment of a suture 200 that includes a plurality of directional indicators 202a, 202b, 202c in the form of arrows having a "V" shape. Similar to that discussed above regarding the suture 10 of FIGS. 1-3, the directional indicators 202a, 202b, 202c in different ones of the suture's rows 204a, 204b, 204c are identified by different reference numeral suffixes. A fourth row of directional indicators that is 90° radially offset around the suture's circumference from the first and third rows 204a, 204c is obscured in FIG. 5. In this illustrated embodiment, the suture 200 is formed of sixteen threads braided together, with twelve of the threads being of a first color and forming a background of the suture's external surface and four of the threads being of a second color and forming the directional indicators 202a, 202b, 202c of the suture's external surface.

The directional indicators 202a, 202b, 202c being formed as an integral part of the suture 200 can allow the suture 200 to include the directional indicators 202a, 202b, 202c along an entire longitudinal length thereof. FIG. 5 shows one free end 206 of the suture 200 and the directional indicators 202a, 202b, 202c extending along the suture's longitudinal length to the free end 206. The directional indicators 202a, 202b, 202c can similarly extend to the suture's other free end (not shown).

The suture 200 can include transitional regions 208 between directional indicators 202a, 202b, 202c in adjacent ones of the rows 204a, 204b, 204c. The transitional regions 208 indicate areas in which the threads of the first color, e.g., background threads, overlay the threads of the second color, e.g., directional indicator threads, in the braid that forms the suture 200. If the first color is not sufficiently dark enough to entirely obscure the threads of the second color underlying threads of the first color, the transitional regions 208 can be visually discernable by a user looking at the suture's external surface. The directional indicators 202a, 202b, 202c can nevertheless be easily visually discernable by viewing the suture's external surface. In some embodiments, the first color can be sufficiently dark to entirely obscure the second color underlying threads of the first color in some situations but not be sufficiently dark enough in other situations, e.g., if the suture is viewed under brighter light. The transition regions 208 may thus be visible in some situations but not be visible in other situations.

FIGS. 6-9 illustrate another embodiment of a suture 300 that includes a plurality of directional indicators in the form of arrows having a "V" shape. Only two of the directional indicators 302a, 302b have reference numerals pointing thereto in FIGS. 6-9 for clarity of illustrating relative positions of the directional indicators 302a, 302b. Each of the directional indicators 302a, 302b is in one of two of the suture's rows 304a, 304b. In this illustrated embodiment, the suture 300 is formed of eight threads braided together, with six of the threads being of a first color and forming a background of the suture's external surface and two of the threads being of a second color and forming the directional indicators 302a, 302b of the suture's external surface.

The suture 300 in this illustrated embodiment includes transitional regions between directional indicators in the adjacent rows 304a, 304b. Only one of the transitional regions 306 has a reference numeral pointing thereto in FIGS. 7-9 (the transitional region 306 is obscured in FIG. 6) for clarity of illustrating relative positions of the labeled directional indicators 302a, 302b in FIGS. 7-9 with respect to the transitional region 306.

Figure 6:
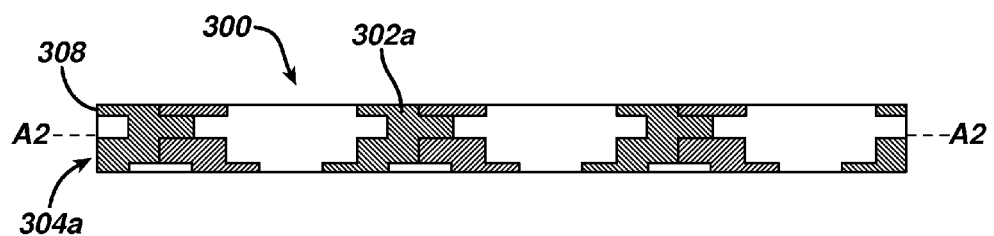
FIG. 6 is a side schematic view of yet another embodiment of a suture that includes directional indicators.
Figure 7:
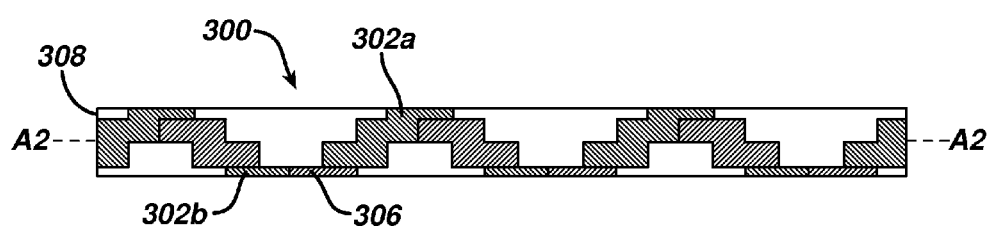
FIG. 7 is a side schematic view of the suture of FIG. 6 rotated 60° about a longitudinal axis of the suture.
Figure 8:
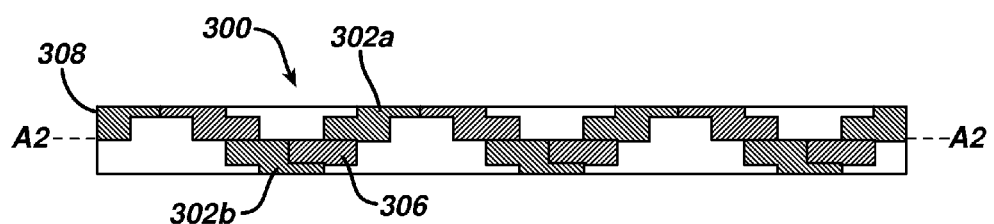
FIG. 8 is a side schematic view of the suture of FIG. 7 rotated 60° about the longitudinal axis of the suture.
Figure 9:
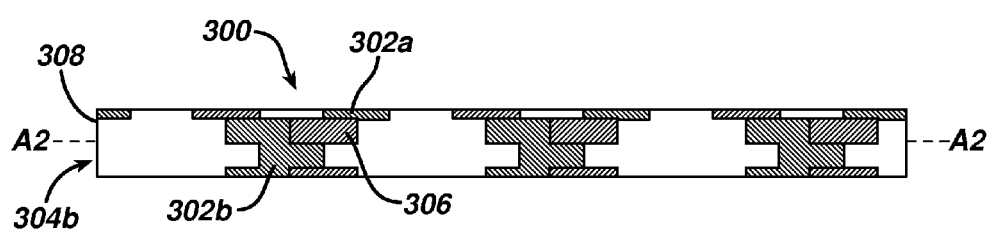
FIG. 9 is a side schematic view of the suture of FIG. 8 rotated 60° about the longitudinal axis of the suture.

FIG. 7 shows the suture 300 rotated 60° about its longitudinal axis A2 from the suture 300 of FIG. 6. FIG. 8 shows the suture 300 rotated 60° about its longitudinal axis A2 from the suture 300 of FIG. 7. FIG. 9 shows the suture 300 rotated 60° about its longitudinal axis A2 from the suture 300 of FIG. 8 and hence shows the suture 300 rotated 180° from the suture 300 of FIG. 6. Because the suture 300 includes only two rows 304a, 304b of directional indicators, the direction in which the directional indicators point may not be entirely clear depending on a vantage point of viewing the suture 300. For example, it may not be clear from the vantage points of the suture 300 shown in FIGS. 7 and 8 that the suture's directional indicators point away from a free end 308 of the suture 300 and toward an opposite free end (not shown) of the suture 300. Thus, sutures including only two rows of directional indicators can have relatively small diameters, as compared with other sutures, so as to help minimize chances of the direction of the directional indicators not being visually discernable from certain vantage points of the suture.

The sutures disclosed herein can be braided. The braid of the suture can have any braid thread density, as will be appreciated by a person skilled in the art, as appropriate for various uses of the suture. For example, a braided suture can have picks per inch (PPI), e.g., number of thread crosses in an inch of suture length, in a range of about 59 to 65 PPI, e.g., about 62 PPI.

The sutures disclosed herein can be braided using a braiding machine. The braiding machine can braid sutures at a relatively high speed, can braid sutures with consistency from one suture to another, and can be much less likely to tangle a plurality of threads while braiding the threads than a human manually braiding the threads. A variety of braiding machines can be used to form a suture having a plurality of directional indicators.

The braiding machine can include a plurality of bobbins, also referred to as "carriers" or "spools," each configured to be wound with a thread. The braiding machine can also include a plurality of gears, e.g., horn gears (also referred to as "notched gears"), each configured to carry at least one of the bobbins. Rotational movement of the gears carrying the bobbins can cause the threads to unwind from the bobbins in a predetermined pattern and form a braided suture, as discussed further below. In an exemplary embodiment, the braiding machine can include a circular braiding machine configured to braid threads together to form a suture having a circular cross-sectional shape.

Each of the bobbins can have a thread of either a first color or a second color wound therearound in order to form a suture having a background of the first color and having a plurality of directional indicators of the second color. The positional relationships of the bobbins having the first color thread and the bobbins having the second color thread can cause a suture braided using the first and second color threads to have directional indicators as disclosed herein. As mentioned above, however, more than two colors can be used to form a suture.

The gears can be arranged around a perimeter of a shape such that each of the gears is adjacent to two others of the gears. In an exemplary embodiment, the gears can be arranged around a perimeter of a circle, thereby allowing a suture made using the gears to have a circular cross-sectional shape. Each of the gears can be configured to rotate, e.g., rotate about a central axis thereof, similar to a record on a record player, relative to at least one other of the gears. The bobbins can be configured to be carried by different ones of the gears as the gears rotate so as to allow the threads to unwind from the bobbins and braid together, as discussed further below.

The braiding machine can include a base that seats each of the plurality of gears. The base can have a variety of shapes. The gears can be arranged around the perimeter of the base's shape. In an exemplary embodiment, the base can have a circular shape such that a perimeter of the base is circular.

Figure 10:
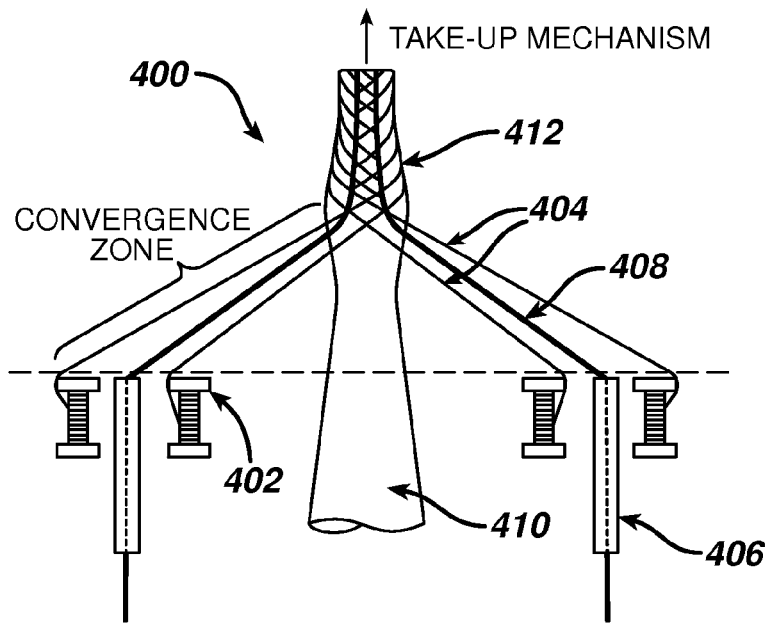
FIG. 10 (Prior Art) is a side schematic view of one embodiment of a braiding machine.
Figure 11:
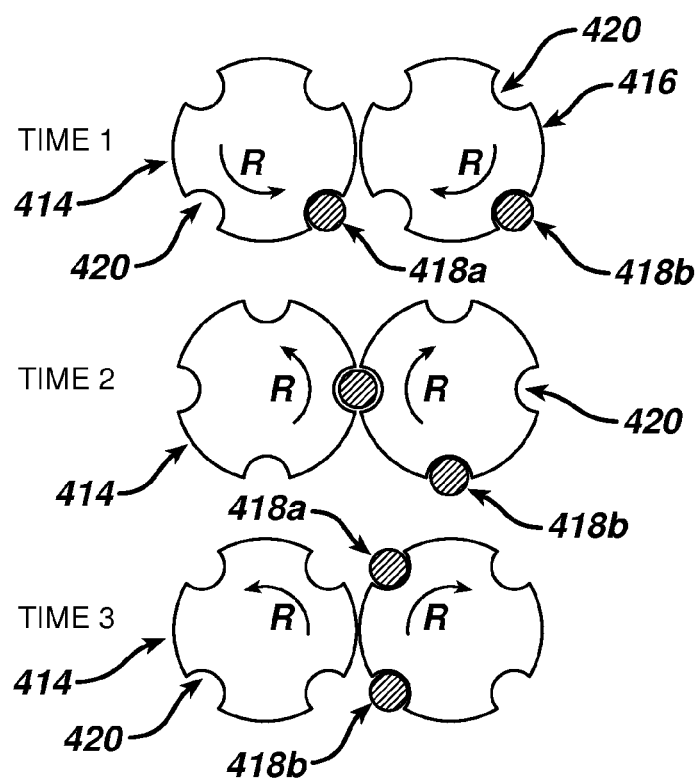
FIG. 11 (Prior Art) is a top schematic view of one embodiment of horn gears of the braiding machine of FIG. 10 in rotational positions at three successive times.

FIG. 10 illustrates an example of a conventional circular braiding machine 400 that includes a plurality of bobbins 402 each having a braiding yarn 404 wound therearound, a plurality of optional tubes 406 for optional axial fibers 408, and an optional mandrel 410 (see Peter Popper, "Braiding," Handbook of Composite Reinforcements, Ed. Stuart M. Lee, p. 24-40, 1992). Generally, movement of the bobbins 402 relative to one another can form a braid 412. FIG. 11 illustrates an example of a horn gear mechanism of the braiding machine 400 that includes two horn gears 414, 416 that can rotate in the directions shown by directional arrows R and that can move bobbins 418a, 418b by seating the bobbins 418a, 418b in various notches 420 formed in the gears 414, 416 as the gears 414, 416 rotate (see supra Popper). As the bobbins 418a, 418b move in and out of the various notches 420, threads (not shown in FIG. 11) wound around the bobbins 418a, 418b can unwind and braid together as shown in FIG. 10 (see supra Popper).

Figure 12:
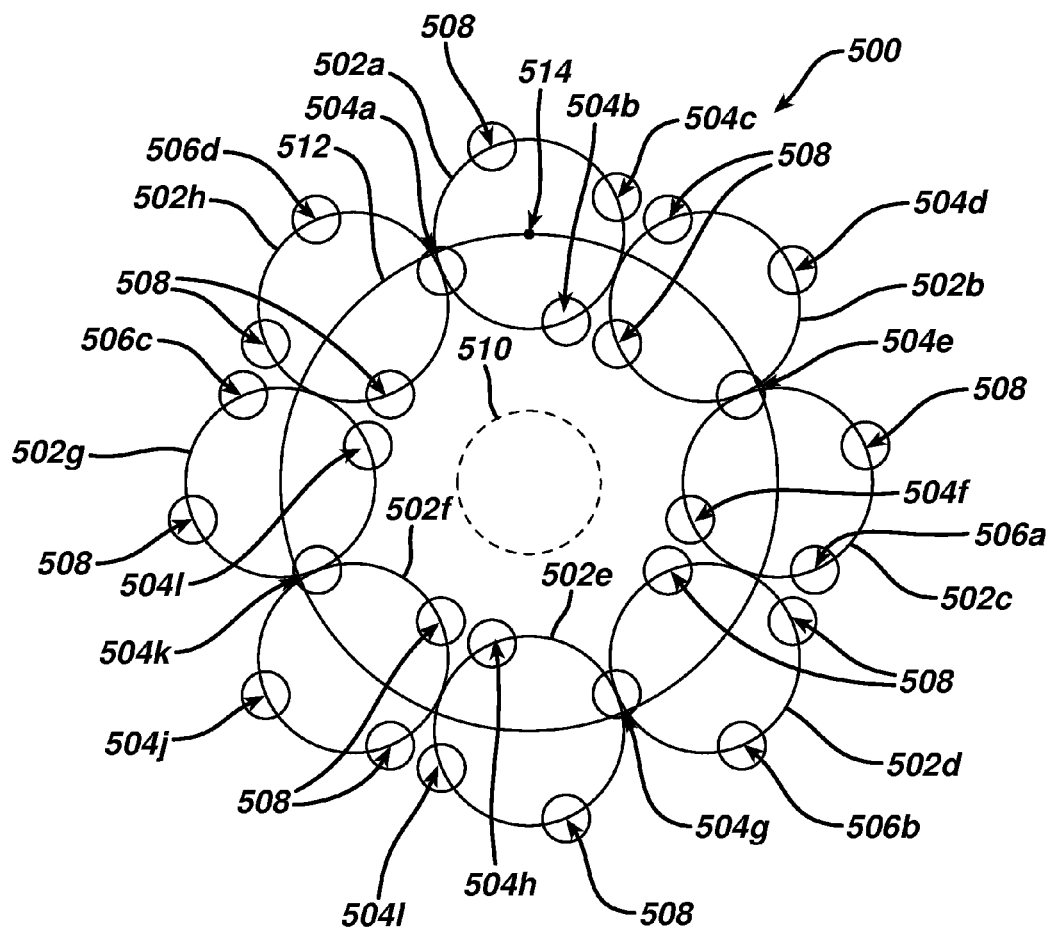
FIG. 12 is a top schematic view of one embodiment of a carrier mechanism of a braiding machine.

FIG. 12 illustrates an embodiment of a carrier mechanism 500 of a circular braiding machine (not shown) that is configured to braid a suture (not shown) having a plurality of directional indicators. The carrier mechanism 500 can include a plurality of horn gears 502a, 502b, 502c, 502d, 502e, 502f, 502g, 502h and a plurality of bobbins configured to be seated in notches formed in the horn gears 502a, 502b, 502c, 502d, 502e, 502f, 502g, 502h.

The horn gears 502a, 502b, 502c, 502d, 502e, 502f, 502g, 502h can each include a circular member having a plurality of notches formed in a perimeter thereof. The notches can be spaced equidistantly around the gear's perimeter, as in the illustrated embodiment. The horn gears 502a, 502b, 502c, 502d, 502e, 502f, 502g, 502h can be positioned in a circular pattern so as to be positioned around a perimeter of a circle with each one of the horn gears 502a, 502b, 502c, 502d, 502e, 502f, 502g, 502h being adjacent to two others of the horn gears 502a, 502b, 502c, 502d, 502e, 502f, 502g, 502h. Edges of adjacent ones of the horn gears 502a, 502b, 502c, 502d, 502e, 502f, 502g, 502h can abut one another so as to facilitate alignment of notches in adjacent ones of the horn gears 502a, 502b, 502c, 502d, 502e, 502f, 502g, 502h and hence facilitate movement of the bobbins 504a, 504b, 504c, 504d, 504e, 504f, 504g, 504h, 504i, 504j, 504k, 504l, 506a, 506b, 506c, 506d between notches in adjacent horn gears as the notches pass by one another during rotation of the gears 502a, 502b, 502c, 502d, 502e, 502f, 502g, 502h.

A first plurality of the bobbins 504a, 504b, 504c, 504d, 504e, 504f, 504g, 504h, 504i, 504j, 504k, 504l can have a thread (not shown) of a first color wound therearound. A second, remaining plurality of the bobbins 506a, 506b, 506c, 506d can have a thread (not shown) of a second color wound therearound. Notches of the horn gears 502a, 502b, 502c, 502d, 502e, 502f, 502g, 502h that do not have a bobbin seated therein are empty notches 508. The carrier mechanism 500 includes sixteen bobbins 504a, 504b, 504c, 504d, 504e, 504f, 504g, 504h, 504i, 504j, 504k, 504l, 506a, 506b, 506c, 506d in this illustrated embodiment, but a carrier mechanism can include another number of bobbins. For example, a carrier mechanism can include more than sixteen bobbins to facilitate forming a suture having a larger diameter and/or a greater number of rows of directional indicators, and a carrier mechanism can include fewer than sixteen bobbins therein to facilitate forming a suture having a smaller diameter and/or a fewer number of rows of directional indicators. As will be appreciated by a person skilled in the art, diameters of the threads can affect an overall diameter of the suture formed using the threads.

FIG. 12 shows the carrier mechanism 500 in an initial loading configuration prior to the braiding machine that includes the carrier mechanism being turned "on" to begin braiding a suture. In other words, the horn gears 502a, 502b, 502c, 502d, 502e, 502f, 502g, 502h have not yet rotated to cause the threads wound around any of the bobbins 504a, 504b, 504c, 504d, 504e, 504f, 504g, 504h, 504i, 504j, 504k, 504l, 506a, 506b, 506c, 506d to unwind and be braided together. In the initial loading configuration in this illustrated embodiment, the horn gears 502a, 502b, 502c, 502d, 502e, 502f, 502g, 502h are arranged around in a circle in an order of half the gears 502c, 502d, 502g, 502h including at least one of the bobbins 506a, 506b, 506c, 506d wound with the second plurality of threads (e.g., the third and fourth gears 502c, 502d), half the gears 502a, 502b, 502c, 502d, 502e, 502f, 502g, 502h including at least one of the bobbins 504a, 504b, 504c, 504d, 504e, 504f, 504g, 504h, 504i, 504j, 504k, 504l wound with the first plurality of threads and none of the bobbins 506a, 506b, 506c, 506d wound with the second plurality of threads (e.g., the fifth and sixth gears 502e, 502f), the other half of the gears 502a, 502b, 502c, 502d, 502e, 502f, 502g, 502h including at least one of the bobbins 506a, 506b, 506c, 506d wound with the second plurality of threads (e.g., the seventh and eighth gears 502g, 502h), and the other half of the gears 502a, 502b, 502c, 502d, 502e, 502f, 502g, 502h including at least one of the bobbins 504a, 504b, 504c, 504d, 504e, 504f, 504g, 504h, 504i, 504j, 504k, 504l wound with the first plurality of threads and none of the bobbins 506a, 506b, 506c, 506d wound with the second plurality of threads (e.g., the first and second gears 502a, 502b).

With the bobbins 504a, 504b, 504c, 504d, 504e, 504f, 504g, 504h, 504i, 504j, 504k, 504l including threads of the first color positioned with respect to the bobbins 506a, 506b, 506c, 506d including threads of the second color and with respect to the empty notches 508 in the initial loading configuration, the threads of the first and second color can be braided together to form the suture having a background of the first color and the plurality of directional indicators of the second color. When the horn gears 502a, 502b, 502c, 502d, 502e, 502f, 502g, 502h loaded with bobbins as shown in FIG. 12 move from the initial loading configuration to a braiding configuration in which the horn gears 502a, 502b, 502c, 502d, 502e, 502f, 502g, 502h are moving such that the bobbins 504a, 504b, 504c, 504d, 504e, 504f, 504g, 504h, 504i, 504j, 504k, 504l, 506a, 506b, 506c, 506d can move between different ones of the horn gears' notches in response to the horn gears' movement, e.g., by moving from the notch in which it is seated to one of the empty notches 508, the suture having the background of the first color and the directional indicators of the second color can be formed. The suture formed using the sixteen threads of the sixteen bobbins 504a, 504b, 504c, 504d, 504e, 504f, 504g, 504h, 504i, 504j, 504k, 504l, 506a, 506b, 506c, 506d in this illustrated embodiment will have four rows of the directional indicators with the rows positioned 90° apart from one another around the suture's circular circumference, similar to the suture 10 of FIGS. 1-3 and the suture 200 of FIG. 5. As will be appreciated by a person skilled in the art, the ones of the notches that have bobbins seated therein and that are empty will change as the horn gears 502a, 502b, 502c, 502d, 502e, 502f, 502g, 502h move and the bobbins get carried between different ones of the horn gears 502a, 502b, 502c, 502d, 502e, 502f, 502g, 502h.

In the embodiment of FIG. 12, the threads wound around the bobbins 504a, 504b, 504c, 504d, 504e, 504f, 504g, 504h, 504i, 504j, 504k, 504l, 506a, 506b, 506c, 506d are not braided around a core. To form a suture having a core, a core 510, shown in phantom in FIG. 12, can be positioned within the perimeter of the shape around which the horn gears 502a, 502b, 502c, 502d, 502e, 502f, 502g, 502h are positioned. The threads can thus unwind and be braided around the core 510.

The carrier mechanism 500 can include a base 512 configured to seat each of the horn gears 502b, 502c, 502d, 502e, 502f, 502g, 502h. The base 512 can define the perimeter around which the horn gears 502b, 502c, 502d, 502e, 502f, 502g, 502h are positioned. In the illustrated embodiment, the base 512 has a circular shape that defines the circular positioning of the horn gears 502a, 502b, 502c, 502d, 502e, 502f, 502g, 502h. The base 512 can have a variety of configurations, such as a plate or a cylinder, as will be appreciated by a person skilled in the art.

Each of the horn gears 502a, 502b, 502c, 502d, 502e, 502f, 502g, 502h can be configured to move relative to the base 512 so as to cause unwinding of the threads and movement of the bobbins 504a, 504b, 504c, 504d, 504e, 504f, 504g, 504h, 504i, 504j, 504k, 504l, 506a, 506b, 506c, 506d between different ones of the notches. Each of the horn gears 502b, 502c, 502d, 502e, 502f, 502g, 502h can be configured to rotate relative to the base 512 about its central axis. A central axis 514 for the first horn gear 512a is shown in FIG. 12. The horn gears 502a, 502b, 502c, 502d, 502e, 502f, 502g, 502h can be configured to each rotate at a same constant velocity, which can help form a secure braid having a consistent diameter and pattern of directional indicators along its longitudinal length. A person skilled in the art will appreciate that the velocity may not be precisely the same for each of the horn gears 502a, 502b, 502c, 502d, 502e, 502f, 502g, 502h due to, for example, manufacturing tolerances in diameters of the horn gears 502a, 502b, 502c, 502d, 502e, 502f, 502g, 502h, but nevertheless be considered to be the same velocity. A first number of the horn gears 502a, 502c, 502e, 502g can be configured to rotate clockwise, and a second, remaining number of the horn gears 502b, 502d, 502f, 502h can be configured to rotate counterclockwise.

Each of the horn gears 502a, 502b, 502c, 502d, 502e, 502f, 502g, 502h can be attached to the base 512 at a point through which its central axis passes, e.g., a center of the circle defined by the horn gear, which can facilitate rotation of the horn gears 502a, 502b, 502c, 502d, 502e, 502f, 502g, 502h about their central axes relative to the base 512. As will be appreciated by a person skilled in the art, the braiding machine can include at least one motor and/or other mechanism (not shown) configured to impart motion to the horn gears 502a, 502b, 502c, 502d, 502e, 502f, 502g, 502h.

As mentioned above, the sutures disclosed herein can be used in a variety of medical procedures. A person skilled in the art will appreciate that the sutures discloses herein have application in conventional minimally-invasive and open surgical instrumentation as well application in robotic-assisted surgery. In some embodiments, a suture including directional indicators can be used to pull a graft at least partially into a tunnel formed in bone. The directional indicators can indicate the direction in which the suture should be pulled to pull the graft into the tunnel, as opposed to being pulled away from the tunnel.

Figure 13:
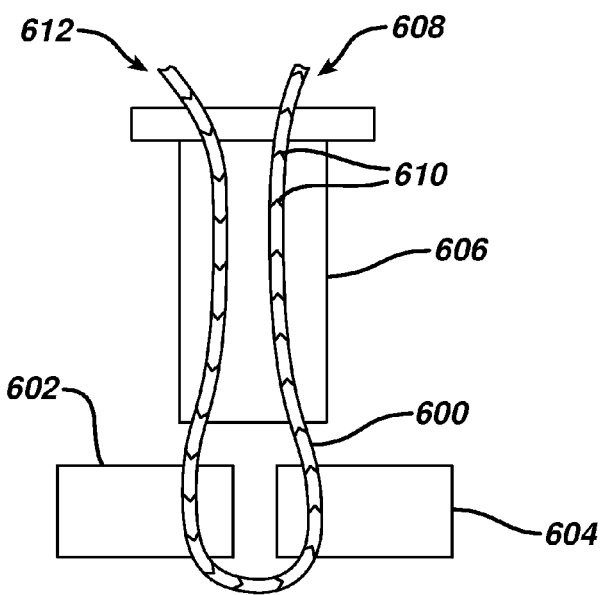
FIG. 13 is a side schematic view of one embodiment of a suture that includes directional indicators positioned through a cannula and through two soft tissues.

FIG. 13 illustrates an embodiment of a suture 600 in use in a medical procedure in which first and second tissues 602, 604 of a patient can be approximated together. The suture 600 can be introduced into a body of the patient in any way, as will be appreciated by a person skilled in the art, and can be passed through the first and second tissues 602, 604 in any way, as will also be appreciated by a person skilled in the art. In this illustrated embodiment, the suture 600 is passed through a cannula 606 and into the patient's body. In order to pull the tissues 602, 604 together, a first free end 608 of the suture 600 can be pulled in a proximal direction, e.g., in a direction away from the cannula 606. Directional indicators 610 of the suture 600 can indicate that the first free end 608 of the suture 600 should be pulled to approximate the tissues 602, 604, as opposed to pulling a second free end 612 of the suture 600. A plurality of the directional indicators 610 can be visible outside the patient's body, e.g., proximal to the cannula 606, which can facilitate easy identification of the free end 608 to pull.

Figure 14:
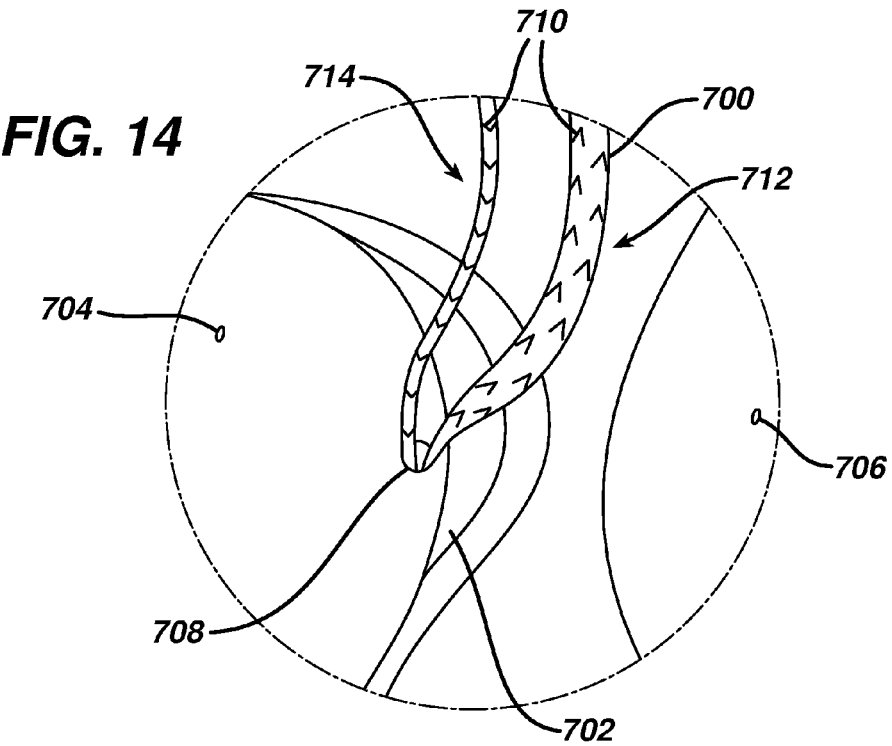
FIG. 14 is a top schematic view of one embodiment of a suture that includes directional indicators coupled to a suture anchor inserted into a glenoid rim of a glenoid.

FIG. 14 illustrates an embodiment of a suture 700 in use in an arthroscopic medical procedure involving labral repair that attempts to repair a tear 702 of a labrum of a patient. For clarity of illustration, FIG. 14 shows a surface 704 of the patient's glenoid and the patient's humeral head 706. A suture anchor 708 has been inserted into a glenoid rim of the glenoid, but the suture 700 has not been passed through the torn labrum. Directional indicators 710 of the suture 700 can help indicate which portion of the suture 700 coupled to the suture anchor 708 and extending therefrom should be passed through the torn labrum, namely a first limb 712 extending from the anchor 708 or a second limb 714 extending from the anchor 708. The second limb 714 can be knotted (not shown) such that the first limb 712 is the limb which should be passed through the torn labrum in order for the tear 702 to be properly repaired. However, the knot may not be visible under arthroscopic vision, as reflected in FIG. 14. The directional indicators 710 on the first limb 712 can indicate a portion of the suture 700 extending away from the anchor 708 and hence indicate the correct limb to pass through the torn labrum and to pull to close the tear 702. Even without having arthroscopic vision of the knot, the correct limb 712 can thus be identified based on the directional indicators 710.

The braiding techniques to form the sutures disclosed herein can, as discussed above, be particularly useful to form sutures for use in medical applications. However, the braiding techniques disclosed herein can forms devices that have applications outside a medical context. For example, the braiding techniques disclosed herein can be used to form a rope having a plurality of directional indicators. The rope can be useful in a variety of applications in which the rope providing an indication of which direction to pull the rope can be useful, such as in rock climbing and in sailing. To form a rope including directional indicators, a braiding machine can be loaded with bobbins including threads of appropriate strength, thickness, etc., some of the threads being of a first color and some of the threads being of a second color. Similar to that discussed above with respect to FIG. 12, the bobbins wound with the first and second colors can be arranged in an initial loading configuration, and the braiding machine can form a rope using the threads.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims.

What is claimed is:

1. A surgical device, comprising:
a suture configured to engage tissue of a patient, the suture including a first plurality of threads of a first color and a second plurality of threads of a second color, the first plurality of threads being braided with the second plurality of threads such that directional arrows formed only from the second plurality of threads are present on an external surface of the suture and are visually discernable by a human user of the suture, all of the directional arrows pointing in a same direction.

2. The device of claim 1, wherein the directional arrows include a first row of directional arrows longitudinally aligned along a longitudinal length of the suture and a second row of directional arrows longitudinally aligned along the longitudinal length of the suture.

3. The device of claim 2, wherein the first and second rows are positioned 180° apart from one another around a circumference of the suture.

4. The device of claim 2, wherein the directional arrows include a third row of directional arrows longitudinally aligned along the longitudinal length of the suture and a fourth row of directional arrows longitudinally aligned along the longitudinal length of the suture.

5. The device of claim 4, wherein the first, second, third, and fourth rows are positioned 90° apart from adjacent ones of the rows around a circumference of the suture.

6. The device of claim 1, wherein a number of the first plurality of threads is greater than a number of the second plurality of threads.

7. The device of claim 1, wherein a number of the first plurality of threads is three times a number of the second plurality of threads.

8. The device of claim 1, wherein the directional arrows are the only portion of the external surface of the suture formed by the second plurality of threads.

9. The device of claim 1, wherein the suture is flexible.

10. A surgical method, comprising:
coupling the suture of claim 1 to the tissue such that first and second free lengths of the suture extend from the tissue, the first free length having the directional arrows thereon pointing toward the tissue and the second free length having the directional arrows thereon pointing away from the tissue; and
after coupling the suture to the tissue, pulling the second free length of the suture in the direction in which the directional arrows thereon point so as to tighten the suture relative to the tissue.

11. A surgical device, comprising:
a suture configured to engage tissue of a patient, the suture including a first plurality of threads of a first color and a second plurality of threads of a second color that visually contrasts with the first color, the first plurality of threads being braided with the second plurality of threads such that the second plurality of threads form a pattern of arrows on an external surface of the suture, all of the arrows pointing in a same direction toward one free end of the suture, and the second color visually contrasting with the first color allowing the plurality of arrows to be visually discernable by a human user of the suture.

12. The device of claim 11, wherein the directional arrows are an integral part of the suture and are formed only from the second plurality of threads.

13. The device of claim 11, wherein the arrows include a plurality of rows of arrows, the arrows in each of the rows being longitudinally aligned along a longitudinal length of the suture.

14. The device of claim 13, wherein the rows are spaced equidistantly from each other around a circumference of the suture.

15. The device of claim 11, wherein the pattern of arrows is the only portion of the external surface of the suture formed by the second plurality of threads.

16. The device of claim 11, wherein the suture is flexible.

17. A surgical method, comprising:
coupling the suture of claim 11 to the tissue such that first and second free lengths of the suture extend from the tissue, the first free length having the arrows thereon pointing toward the tissue, the second free length having the arrows thereon pointing away from the tissue, and the one free end of the suture being a terminal end of the second free length of the suture; and
after coupling the suture to the tissue, pulling the second free length of the suture in the direction in which the arrows thereon point so as to tighten the suture relative to the tissue.

18. A method of creating a suture, comprising:
braiding a first plurality of threads of a first color with a second plurality of threads of a second color so as to create a suture configured to engage tissue of a patient, wherein
the suture has a plurality of arrows on an external surface thereof that are entirely formed with the second plurality of threads,
all of the arrows point in a same direction,
the braiding uses a plurality of gears,
the gears are arranged around a perimeter of a shape such that each of the gears is adjacent to two others of the gears,
each of the gears rotates in an opposite direction to its two adjacent gears when braiding the suture,
each of the gears seats at least one bobbin having one of the threads wound therearound,
an even number of the bobbins is wound with the second plurality of threads, and a remaining number of the bobbins is wound with the first plurality of threads, and
the gears are arranged around the perimeter of the shape in an order of half the gears including at least one of the bobbins wound with the second plurality of threads, half the gears including at least one of the bobbins wound with the first plurality of threads and no bobbins wound with the second plurality of threads, the other half of the gears including at least one of the bobbins wound with the second plurality of threads, and the other half of the gears including at least one of the bobbins wound with the first plurality of threads and no bobbins wound with the second plurality of threads.

19. The method of claim 18, wherein a ratio of the even number of the bobbins to the remaining number of the bobbins is 1:3.

20. A medical device comprising the suture formed by the method of claim 18.

* * * * *